(12) United States Patent
  Ostendorf et al.

(10) Patent No.: US 12,569,442 B2
(45) Date of Patent: Mar. 10, 2026

(54) PROCESS FOR PRODUCING A PHARMACEUTICAL FORMULATION COMPRISING ACTIVE SUBSTANCE, POLYMER AND SURFACTANT

(71) Applicant: Bayer Aktiengesellschaft, Leverkusen (DE)

(72) Inventors: Michael Ostendorf, Leverkusen (DE); Werner Hoheisel, Cologne (DE); Bjoern Duesenberg, Spardorf (DE); Christoph Nueboldt, Heessen (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 886 days.

(21) Appl. No.: 17/761,480

(22) PCT Filed: Oct. 5, 2020

(86) PCT No.: PCT/EP2020/077790
  § 371 (c)(1),
  (2) Date: Mar. 17, 2022

(87) PCT Pub. No.: WO2021/069350
  PCT Pub. Date: Apr. 15, 2021

(65) Prior Publication Data
  US 2022/0370358 A1    Nov. 24, 2022

(30) Foreign Application Priority Data
  Oct. 10, 2019    (EP) .................................... 19202458

(51) Int. Cl.
  *A61K 9/16*    (2006.01)
  *A61K 9/19*    (2006.01)
      (Continued)

(52) U.S. Cl.
  CPC .......... *A61K 9/1635* (2013.01); *A61K 9/1617* (2013.01); *A61K 9/1694* (2013.01);
      (Continued)

(58) Field of Classification Search
  None
  See application file for complete search history.

(56) References Cited

U.S. PATENT DOCUMENTS

2005/0063913 A1*   3/2005   Pruitt ..................... A61K 9/145
                                                           424/452
2011/0064812 A1     3/2011   Bahl et al.
      (Continued)

FOREIGN PATENT DOCUMENTS

CN        101 606 906 A1    12/2009
JP        2014 177415 A1     9/2014
      (Continued)

OTHER PUBLICATIONS

W. Duangkhamchan, F. Ronsse, S. Siriamornpun, and J.G. Pieters. "Numerical study of air humidity and temperature distribution in a top-spray fluidised bed coating process." Journal of Food Engineering, vol. 146, 2015, pp. 81-91. (Year: 2015).*
      (Continued)

*Primary Examiner* — Isaac Shomer
(74) *Attorney, Agent, or Firm* — Ann H. Inglett

(57)    ABSTRACT

A process for producing a pharmaceutical formulation comprises the steps of:
A) suspending a pharmaceutical active substance in an aqueous solution of a polymer;
B) drying the mixture obtained in step A);
wherein in step A) the pharmaceutical active substance is present in the form of particles having a $d_{90}$ value in the
      (Continued)

particle size distribution of ≤1 µm and before step B) the pharmaceutical active substance is further contacted with an ionic surfactant.

10 Claims, 13 Drawing Sheets

(51) Int. Cl.
  *A61K 31/405* (2006.01)
  *A61K 31/506* (2006.01)
(52) U.S. Cl.
  CPC .............. *A61K 9/19* (2013.01); *A61K 31/405* (2013.01); *A61K 31/506* (2013.01)

(56) References Cited

U.S. PATENT DOCUMENTS

2012/0135048 A1* 5/2012 Dodd ..................... A61K 9/143
                                                    514/420
2013/0295190 A1* 11/2013 Bilgili .................. A61K 9/5161
                                                    427/2.16
2016/0245990 A1* 8/2016 Boyden ................ A61N 5/0601
2019/0103200 A1* 4/2019 Hui .......................... H01B 1/22

FOREIGN PATENT DOCUMENTS

WO        2007107222  A1    9/2007
WO        2011/102787  A1    8/2011

OTHER PUBLICATIONS

Anagha Bhakay, Rajesh Davé, Ecevit Bilgili. "Recovery of BCS Class II drugs during aqueous redispersion of core-shell type nanocomposite particles produced via fluidized bed coating." Powder Technology, vol. 236, 2013, pp. 221-234. (Year: 2013).*

Ana M. Cerdeira, Marco Mazzotti, Bruno Gander. "Formulation and drying of miconazole and itraconazole nanosuspensions." International Journal of Pharmaceutics, vol. 443, 2013, pp. 209-220. (Year: 2013).*

International Search Report received in international application No. PCT/EP2020/077790, mailed Oct. 26, 2020, 3 pages.

Cerdeira et al., "Formulation and drying of miconazole and itraconazole nanosuspensions," International Journal of Pharmaceutics, (2013), vol. 443, No. 1: 209-220.

Zuo et al., "Preparation and in vitro/ in vivo evaluation of fenofibrate nanocrystals," International Journal of Pharmaceutics, (2013), vol. 455, No. 1: 267-275.

Chaubal et al., "Conversion of Nanosuspensions into Dry Powders by Spray Drying: A Case Study", Pharmaceutical Research, vol. 25, No. 10, Oct. 2008, pp. 2302-2308.

Dolenc et al., "Advantages of celecoxib nanosuspension formulation and transformation into tablets", International Journal of Pharmaceutics, vol. 376, (2009), pp. 204-212.

Cerdeira et al. "Formulation and drying of miconazole and itraconazole nanosuspensions." International journal of pharmaceutics 443, No. 1-2 (2013): 209-220.

Wang et al. "Stability of nanosuspensions in drug delivery", Journal of Controlled Release 172 (2013) 1126-1141.

Beirowski et al. "Freeze-drying of nanosuspensions, 1: freezing rate versus formulation design as critical factors to preserve the original particle size distribution." Journal of pharmaceutical sciences 100, No. 5 (2011): 1958-1968.

Khinast et al., "Nano-extrusion: a One-Step Process for Manufacturing of Solid Nanoparticle 25 Formulations Directly from the Liquid Phase," AAPS PharmSciTech, vol. 14, No. 2, Jun. 2013, pp. 601-604.

* cited by examiner

PROCESS FOR PRODUCING A PHARMACEUTICAL FORMULATION COMPRISING ACTIVE SUBSTANCE, POLYMER AND SURFACTANT

CROSS-REFERENCE TO RELATED APPLICATIONS

This application is the National Stage entry of International Application No. PCT/EP2020/077790, filed 5 Oct. 2020, which claims priority to European Patent Application No. 192024586, filed 10 Oct. 2019.

BACKGROUND

Field

The present invention relates to a process for producing a pharmaceutical formulation comprising the steps of: A) suspending a pharmaceutical active substance in an aqueous solution of a polymer and B) drying the mixture obtained in step A). The invention likewise relates to a pharmaceutical formulation comprising a pharmaceutical active substance coated with an at least partially water-soluble polymer and to a suspension of a pharmaceutical active substance.

Description of Related Art

A high rate of dissolution of a pharmaceutical active substance usually results in increased bioavailability or at least in improved bioavailability kinetics. This can be achieved, for example, by increasing the specific surface area of the active substance-particle collective. Thus, active substance nanosuspensions have an appreciably higher rate of dissolution than a micronized suspension. In order to produce solid dosage forms, the nanosuspensions must be dried. This often leads to irreversible aggregation of the nanoparticles and thus to a poorer rate of dissolution of the active substance. Drying processes are often freeze-drying and spray-drying or other processes based on spraying the suspensions and other processes based on contact drying, for example drum drying or vacuum drum drying or drying under ambient or reduced pressure. In addition to the usual additives for stabilizing nanosuspensions, such as polymers and surfactants, matrix-forming agents (various sugars and sugar alcohols) are also used here.

Chaubal et al. in "Conversion of Nanosuspensions into Dry Powders by Spray Drying: A Case Study", in Pharmaceutical Research, vol. 25, No. 10, October 2008, reports redispersible powders containing nanoparticles and the importance of charged surfactants in respect of the stability of particles during drying. A disadvantage in this method is that the average particle size of the suspensions after redispersion is always 10-20% greater than in the original suspensions before drying. Moreover, in addition to the stabilizing additives (poloxamer 188 and sodium deoxycholate), matrix-forming agents such as lactose, sucrose and mannitol are used. The particles are also much coarser (99%<1 μm), even before drying (99%<0.8 μm).

Khinast et al. in "Nano-extrusion: a One-Step Process for Manufacturing of Solid Nanoparticle Formulations Directly from the Liquid Phase", in AAPS PharmSciTech, vol. 14, No. 2, June 2013, reported solid nanoparticle-containing formulations produced by extrusion. In this process, the particles were embedded in a polymer matrix. No redispersion experiments were carried out and there was accordingly no discussion of beneficial effects of additives. Moreover, no active substances were used, only inorganic nanoparticles ($TiO_2$).

Wang et al. in "Stability of nanosuspensions in drug delivery", in the Journal of Controlled Release 172(2013) 1126-1141, report powders containing redispersible nanoparticles produced by freeze-drying. Besides the usual stabilizers, additional matrix-forming agents were also used here. SDS is used only as an additive for milling.

Cerdeira et al. in "Formulation and drying of miconazole and itraconazole nanosuspensions", in the International Journal of Pharmaceutics 443 (2013) 209-220, prepared various active substance nanosuspensions containing HPC and SDS, but with concentrations that were too low for the nanoparticle- containing powders to be completely redispersible after drying. Matrix-forming agents (mannitol) are additionally also used here for both spray-drying and freeze-drying. Here too, the beneficial effect on the stability of the nanoparticles during drying is not detected by the constantly low SDS concentration. DISADVANTAGE: No redispersibility without matrix-forming agents, large particles after drying (several micrometres), SDS used only as an additive for milling.

Dolenc ct al (2009) in "Advantages of celecoxib nanosuspension formulation and transformation into tablets", in the International Journal of Pharmaceutics 376 (2009) 204-212, produces nanosuspensions containing PVP and SDS as additives and dries them by spray-drying. A disadvantage of this method is that, although the powders are redispersible, there are clear differences in the x90 value (30%) between the original and redispersed suspensions. The possible benefits of ionic surfactants for the stability of the nanoparticles during drying are not described. SDS serves only as an additive for the formation of stable nanoparticles by precipitation. In addition, much coarser particles are present in the x90 range (>1 μm).

Beirowski et al. (2011) elucidated various mechanisms for the freeze-drying of nanosuspensions and stressed the correct choice of cryoprotectors (for example sugars, sugar alcohols, polymers). Possible effects of ionic surfactants in relation to drying are not described.

WO 2007/107222 A1 claims redispersible nanoparticles that are obtainable from at least one surface- modifying molecule from the group of thiols, sulfides, disulfides or polysulfides and act as free-radical chain-transfer agents. The objective is the functionalization of the surface for further reactions and not redispersibility. Only inorganic particles were used.

US 2011/0064812 A1 claims the method of production in which solid, oral dosage forms (containing active substance nanoparticles) are produced using fish gelatins. The disadvantage here too is that additional matrix-forming agents need to be used. Ionic surfactants are not used.

SUMMARY

The object of the present invention is to provide an improved means of producing powders containing redispersible active substance particles. The particle size distribution (PSD) of the original suspension should be largely maintained after redispersion of the dried powders and aggregation of the nanoparticles prevented.

This object is achieved in accordance with the invention by a process according to claim 1. Advantageous developments are specified in the dependent claims. They may be freely combined unless the opposite is clear from the context.

A process for producing a pharmaceutical formulation comprises the steps of:

A) suspending a pharmaceutical active substance in an aqueous solution of a polymer;

B) drying the mixture obtained in step A);

wherein in step A) the pharmaceutical active substance is present in the form of particles having a $d_{90}$ value in the particle size distribution (PSD, volume-based; determined by laser diffraction in accordance with ISO 13320:2009) of ≤1 μm and before step B) the pharmaceutical active substance is further contacted with an ionic surfactant.

DETAILED DESCRIPTION OF A PREFERRED EMBODIMENT

Figure 1:
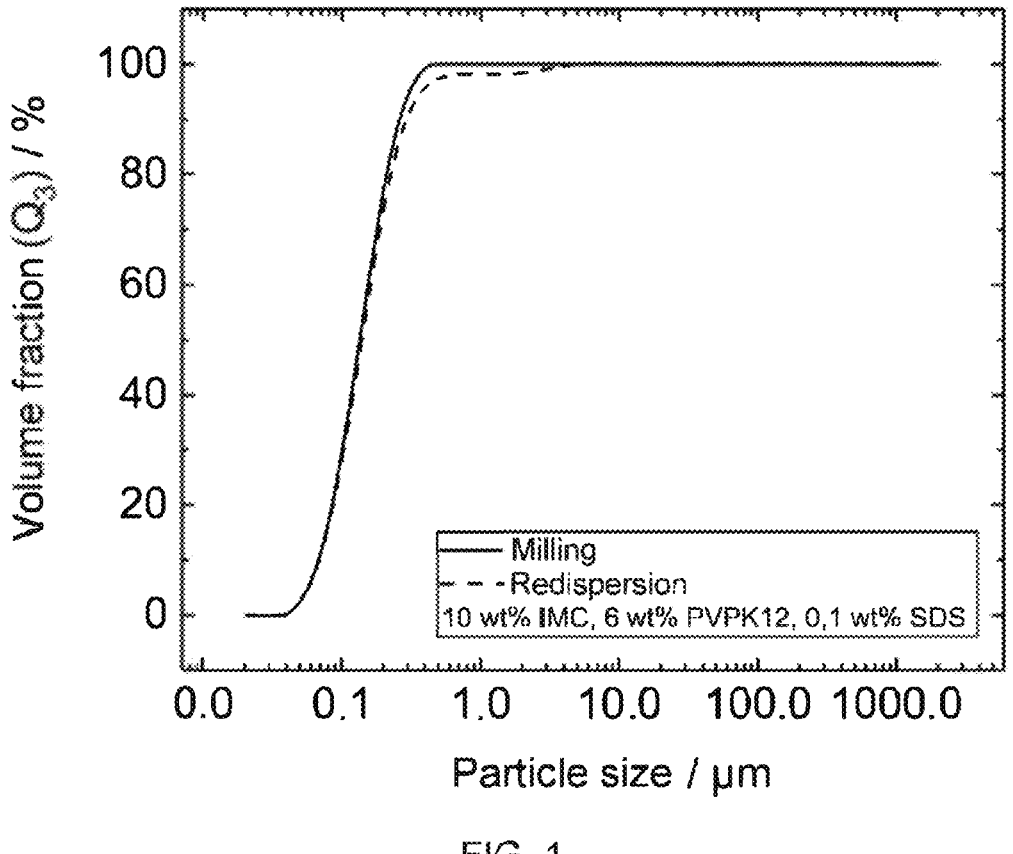
FIGS. 1-13 depict embodiments as described herein.

The present invention enables the process-independent (in relation to the origin of the active substance particles) production of powders containing redispersible active substance nanoparticles. It is a composition that comprises active substance in nanoparticle form and also polymers and ionic surfactants. Additional matrix-forming agents may be dispensed with altogether. The resulting PSD of the suspension formed by rewetting the powders with water corresponds almost exactly to the PSD of the original suspension.

Thus, in the dried mixture obtained in step B) and also in a possible redispersed formulation, the active substance remains present in the form of particles having a $d_{90}$ value in the particle size distribution of <1 μm.

In step A), the active pharmaceutical substance is contacted with an aqueous solution of a polymer. This affords a suspension of the active substance. The term aqueous solution of the polymer also encompasses aqueous gels of the polymer. The polymer is accordingly a water-soluble polymer. "Water-soluble" is understood as meaning that, at 20°° C., at least 0.5 g, preferably at least 2 g, of the polymer dissolves in 100 g of water or dissolves with the formation of a gel.

The polymer may be a neutral polymer or a cationic or anionic polyelectrolyte and may be selected from the following group: alkyl celluloses, hydroxyalkyl celluloses, hydroxyalkyl alkyl celluloses, carboxyalkyl celluloses, alkali metal salts of carboxyalkyl celluloses, carboxyalkyl alkyl celluloses, carboxyalkyl cellulose esters, starches, pectins, chitin derivatives, polysaccharides, polyacrylic acid and salts thereof, polymethacrylic acid and salts thereof, polyvinyl alcohol, polyvinylpyrrolidone, polyalkylene oxides, copolymers of the recited polymer types or a mixture of at least two of the abovementioned polymers.

Examples of suitable active substance classes are benzodiazepines, antihypertensives, vitamins, cytostatics, in particular taxol, anaesthetics, neuroleptics, antidepressants, antiviral agents such as anti-HIV agents, antibiotics, antifungals, anti-dementia agents, fungicides, chemotherapy agents, urologics, platelet- aggregation inhibitors, sulfonamides, spasmolytics, hormones, immunoglobulins, sera, thyroid therapeutics, psychotropic agents, antiparkinsonian agents and other antihyperkinetics, ophthalmics, neuropathy products, calcium-metabolism regulators, muscle relaxants, lipid-lowering agents, liver therapeutics, antianginals, cardiac agents, immunotherapeutics, regulatory peptides and inhibitors thereof, hypnotics, sedatives, gynaecological agents, antigout agents, fibrinolytics, enzyme products and transport proteins, enzyme inhibitors, emetics, blood circulation promoters, diuretics, diagnostics, corticosteroids, cholinergics, biliary therapeutics, antiasthmatics, broncholytics, beta-receptor blockers, calcium-channel blockers, ACE inhibitors, anti-arteriosclerosis agents, anti-inflammatoi anticoagulants, antihypotensives, antihypoglycaemics, antihypertensives, antifibrinolytics, antiepileptics, anticmetics, antidotes, antidiabetics, antiarrhythmics, antianaemics, antiallergics, anthelmintics, analgesics, analeptics, aldosterone antagonists, weight-reduction agents or mixtures of at least two of the abovementioned active substance classes. If the time interval between suspending and drying is appropriately brief, a water-soluble active substance that does not dissolve in the time available may also be used. However, the active substance is preferably water-insoluble, i.e. less than 2 g and more preferably less than 0.5 g, of the active substance dissolves in 100 g of water at 20° C.

As regards the particle size of the active substance, it is preferable that the $d_{90}$ value of the particle size distribution ($d_{90}$ means that 90% of all particles have a diameter no greater than this value; the determination is carried out by laser diffraction in accordance with ISO 13320:2009) is ≥10 nm to ≤1 μm, preferably ≥50 nm to ≤500 nm and more preferably ≥30 nm to ≤300 nm.

The ionic surfactant may be an anionic, cationic or zwitterionic (amphoteric) surfactant. Without being bound to any particular theory, it is assumed that the ionic surfactant in combination with the polymer has a beneficial effect on the stability of the active substance particles during drying. The combination of electrostatic and steric stabilization accordingly makes it possible to redisperse the particles almost completely. It can also be observed that the particles remain in a polymorphic state. This can be documented by X-ray powder diffractometry and by Fourier-transform infrared spectroscopy.

The dosage of the individual components in step A) may, for example, be such that the polymer content is ≥0.1% to ≤40% by weight and the surfactant content ≥0.001% to ≤10% by weight, in each case based on the total weight of the suspension in step A). A further example of a dosage is a ratio by weight of active substance:polymer:surfactant of ≥0.01 to ≤5:1:≥0.001 to ≤1.

The drying in step B) may be carried out for example by freeze-drying, spray-drying, in a rotary evaporator or generally in a contact drying process. After drying and redispersion in aqueous media that do not bring about complete molecular dissolution of the active substance, the particle size distribution (PSD) of the original suspension preferably differs by comparison with the PSD of the redispersed powder only by a factor X within a range from >1 to <3, based on the $d_{90}$ value of the respective suspensions. X here 30 corresponds to the ratio n/v, where n represents the $d_{90}$ value of the PSD after drying and redispersion and v the dou value before drying. X is particularly preferably ≥1 to ≤1.2.

In a further embodiment, the pharmaceutical active substance is selected from: ciclosporin A, ciclosporin G, rapamycin, tacrolimus, deoxyspergualin, mycophenolate mofetil, gusperimus; acetylsalicylic acid, ibuprofen, S (+)-ibuprofen, indometacin, diclofenac, piroxicam, meloxicam, tenoxicam, naproxen, ketoprofen, flurbiprofen, fenoprofen, felbinac, sulindac, etodolac, oxyphenbutazone, phenylbutazone, nabumetone; nifedipine, nitrendipine, nimodipine, nisoldipine, isradipine, felodipine, amlodipine, nilvadipine, lacidipine, benidipine, lercanidipine, furnidipine, niguldipine; a-lipoic acid; muramyl dipeptide or tripeptide, romurtide; vitamin A, D, E or F; vincopectin, vincristine, vinblastine, reserpine, codeine; bromocriptine, dihydroergotamine, dihydroergocristine; chlorambucil, etoposide, teniposide, idoxifene, tallimustine, teloxantrone, tirapazamine, carzelesin, dexniguldipine, intoplicine, idarubicin, miltefosine, trofosfamide, melphalan, lomustine, 4,5-bis (4-fluoroanilino) phthalimide; 4,5-dianilinophthalimide; thymoctonan, prezatide-copper acetate; crythromycin, daunorubicin, gramicidin, g doxorubicin, amphotericin B, gentamicin, leucomycin, streptomycin, ganefromycin, rifamexil, ramoplanin, spiramycin;

fluconazole, ketoconazole, itraconazole; famotidine, cimetidine, ranitidine, roxatidine, nizatidine, omeprazolc; N-[4-mcthyl-3-(4-pyridin-3-ylpyrimidin-2-ylamino) phenyl]benzamide, N-benzoylstaurosporine; BOC-PhecPhe-Val-Phe-morpholine or the O-[2-(2-methoxyethoxy) acetoxy] derivative thercof; N-[4-(5-cyclopentyloxycarbo-nylamino-1-methylindol-3-ylmcthyl)-3-methoxybenzoyl]-2-vinyloxy] benzenesulfonamide or a mixture of at least two of the abovementioned active substances.

In a further embodiment, the polymer is selected from: methyl cellulose, hydroxymethyl cellulose, hydroxyethyl cellulose, hydroxypropyl cellulose, hydroxybutyl cellulose, hydroxyethyl methylcellulose, hydroxypropyl methylcellulose, carboxymethyl cellulose, sodium carboxymethyl cellulose, carboxymethyl cthyl cellulose, carboxyalkyl cellulose esters, starches, sodium carboxymethyl amylopectin, chitosan, alginic acid, alkali metal salts and ammonium salts of alginic acid, carrageenans, galactomannans, tragacanth, agar-agar, gum arabic, guar gum, xanthan gum, polyacrylic acid and salts thereof, polymethacrylic acid and salts thereof, polyvinyl alcohol, polyvinylpyrrolidonc, polyethyl-enc oxidc, polypropylene oxide, copolymers of ethylene oxide and propylene oxide, N-vinylpyrrolidone-vinyl acetate copolymers or a mixture of at least two of the abovementioned polymers. Particular preference is given to polyvinylpyrrolidones (in particular K12 and K30 types) and N-vinylpyrrolidone-vinyl acctate copolymers.

In a further embodiment, the ionic surfactant is selected from:

acylamino acids (and salts thereof), such as: acylglutamates, for example sodium acylglutamate, di-TEA-palmitoyl aspartate and sodium capryl glutamate; acyl peptides, for example palmitoyl-hydrolysed milk protein, sodium cocoyl-hydrolysed soy protein and sodium/potassium cocoyl-hydrolysed collagen; sarcosinates, for example myristoyl sarcosinate, TEA-lau-royl sarcosinate, sodium lauroyl sarcosinate and sodium cocoyl sarcosinate; taurates, for example sodium lauroyl taurate and sodium methyl cocoyl tau-rate; acyl lactylates, lauroyl lactylate, caproyl lactylate, alaninates; carboxylic acids and derivatives, such as: carboxylic acids, for example lauric acid, aluminium stearate, magnesium alkanolate and zinc undecylenate, ester carboxylic acids, for example calcium stearoyl lactylate and sodium PEG lauramide carboxylate, ether carboxylic acids, for example sodium laureth carboxy-late and sodium PEG cocamide carboxylate;

phosphoric esters and phosphate salts, such as DEA oleth phosphate and dilaureth phosphate; sulfonic acids and sulfonate salts, such as acyl isethionates, for example sodium/ammonium cocoyl isethionate, alkyl aryl sulfonates, alkyl sulfonates, for example sodium coco monoglyceride sulfate, sodium C-olefin sulfonate, sodium lauryl sulfoac-etate and magnesium PEG cocamide sulfate, sulfosucci-nates, for example dioctyl sodium sulfosuccinate, disodium laureth sulfosuccinate, disodium lauryl sulfosuccinate and disodium undecylenamido MEA-sulfosuccinate; and also sulfuric esters, such as alkyl ether sulfates, for example sodium laureth sulfate, ammonium laureth sulfate, magne-sium laureth sulfate, MIPA laureth sulfate, TIPA laureth sulfate, sodium myreth sulfate and sodium C-parcth sulfate, alkyl sulfates, for example sodium lauryl sulfate, ammonium lauryl sulfate and TEA lauryl sulfate.

In accordance with the invention, ionic surfactant(s) may further be advantageously selected from the group of cat-ionic surfactants. Cationic surfactants that may be used advantageously are alkylamines, alkylimidazoles, ethoxy-lated amines, quatemary surfactants and esterquats.

Quaternary surfactants contain at least one N atom that is covalently bonded to 4 alkyl or aryl groups. This results in a positive charge, irrespective of pH. Alkyl betaine, alkyl amidopropyl betaine and alkyl amidopropyl hydroxysultainc are advantageous. Cationic surfactants used according to the invention may additionally be preferably selected from the group of quaternary ammonium compounds, in particular benzyltrialkylammonium chlorides or bromides, for example benzyldimethylstearylammonium chloride, and also alkyltrialkylammonium salts, for example cetyltrimeth-ylammonium chloride or bromide, alkyldimethylhydroxy-ethylammonium chlorides or bromides, dialkyldimethylam-monium chlorides or bromides, alkylamidocthyltrimethylammonium ether sulfates, alkylpyridinium salts, for example laurylpyridinium or cetylpyridinium chloride, imidazoline derivatives and com-pounds having a cationic character such as amine oxides, for example alkyldimethylamine oxides or alkylaminoethyldi-methylamine oxides. The use of cetyltrimethylammonium salts is particularly advantageous.

In accordance with the invention, ionic surfactant(s) may be advantageously selected from the group of amphoteric surfactants.

Amphoteric surfactants that may be used advantageously are: acylethylenediamines or dialkylethylenediamines, for example sodium acylamphoacetates, disodium acylam-phodipropionates, disodium alkylamphodiacetates, sodium acylamphohydroxypropylsulfonates, disodium acylampho-diacetates and sodium acylamphopropionates, and also N-al-kylamino acids, for example aminopropylalkylglutamides, alkylaminopropionic acids, sodium alkylimidodipropionates and lauroamphocarboxyglycinate.

Particular preference as surfactant is given to sodium dodecyl sulfate (SDS), sodium docusate, sodium oleate and/or sodium deoxycholate.

In a further embodiment, the particles of the active substance are not contacted with a sugar or sugar alcohol. Such compounds are used as matrix-forming agents in the prior art and are not necessary in the process according to the invention.

In a further embodiment, the particles of the active substance are present at least partially in crystalline form.

In a further embodiment, the active substance and the polymer are present in a relative weight ratio of $\geq 1:4$ to $\leq 9:1$. In a preferred variant of this embodiment, the active sub-stance and the polymer are present in a relative weight ratio of $\geq 1:2$ to $\leq 5:1$, more preferably $\geq 1:1$ to $\leq 2:1$.

In a further embodiment, the polymer and the surfactant are present in a relative weight ratio of $\geq 10:1$ to $\leq 300:1$ (preferably $\geq 40:1$ to $\leq 100:1$).

In a further embodiment, the active substance was obtained in the form of particles by means of milling.

When the active substance is obtained in the form of particles by means of milling, it is preferable to adhere to a preferred milling time during milling so as to achieve better redispersion of the dried, nanoparticle- containing powder. This preferred milling time (t-preferred) is appreciably longer than the milling time that would normally be required to achieve the necessary particle size.

This preferred milling time (t-preferred) is at least 1.5 times t0, preferably at least 2 times t0 and more preferably at least 4 times t0. to here is the usual milling time at which the $d_{90}$ value of the particle size distribution (PSD) is 1.5 times the de value that is reached after 12 hours and which is termed $d_{90}$ (12 h). In other words, this means that $d_{90}$ (12 h) is ⅔ of the $d_{90}$ value for the usual milling time t0. In this application, the milling time is understood as meaning the residence time of the suspension in the mill, which means explicitly that any time spent by the suspension in a holding tank that is optionally used is not counted towards the milling time, that is to say the comminution time (tc).

It was surprisingly found, that when a preferred milling time is employed, improved redispersion is achieved after drying. The factor X defined above therefore approximates to the ideal value 1 when using a preferred milling time.

In a further embodiment, the active substance was obtained in the form of particles by means of precipitation.

In a further embodiment, the drying in step B) is effected by means of freeze-drying.

In a further embodiment, the drying in step B) is effected by means of a process based on spraying of the active substance suspension. Preference is given to spray-drying.

In an embodiment of the process in which the drying in step B) is effected by means of a process based on spraying of the active substance suspension, the drying temperature does not exceed certain values t. The outlet temperature here (T_out), e.g. in a spray-dryer, is lower than the glass transition temperature (Tg) of the polymer present in the suspension (T_out<Tg). When a polymer mixture is used, the upper temperature limit is the glass transition temperature (Tg) of the particular polymer mixture.

In a preferred embodiment of drying in step B) by means of a process based on spraying of the active substance suspension, in which the drying temperature does not exceed certain values, the outlet temperature (T_out), e.g. in a spray-dryer, is more than 20 K below the glass transition temperature (Tg) of the polymer present in the suspension (T_out<Tg-20 K). When a polymer mixture is used, the upper temperature limit is the temperature 20 K below the glass transition temperature (Tg_mixture) of the particular polymer mixture, i.e. T_out is defined as T_out<Tg_mixture-20 K.

In a particularly preferred embodiment of drying in step B) by means of a process based on spraying of the active substance suspension, in which the drying temperature does not exceed certain values, the outlet temperature (T_out), e.g. in a spray-dryer, is more than 40 K below the glass transition temperature (Tg) of the polymer present in the suspension (T_out<Tg-40 K). When a polymer mixture is used, the upper temperature limit is the temperature 20 K below the glass transition temperature (Tg_mixture) of the particular polymer mixture, i.e. T out is defined as T_out<Tg_mixture-40 K.

The outlet temperature is understood as meaning the temperature of the drying gas on exiting the drying volume.

In a further embodiment, the drying in step B) is effected by means of contact drying. In this process, the suspension is brought into contact with a surface until the suspension has dried to a solid substance. The temperature of the surface (Ts) is lower than the glass transition temperature (Tg) of the polymer present in the suspension (Ts<Tg). When a polymer mixture is used, the upper temperature limit of the surface is the glass transition temperature (Tg) of the particular polymer mixture.

In a preferred embodiment of drying in step B) by means of contact drying, the temperature of the surface (Ts) is 20 K below the glass transition temperature (Tg) of the polymer present in the suspension (Ts<Tg-20 K). When a polymer mixture is used, the upper temperature limit of the surface is the temperature 20 K below the glass transition temperature (Tg) of the particular polymer mixture, i.e. Ts is defined as Ts<Tg-20 K.

In general, an upper temperature limit T_limit applies to drying for all heat-based drying processes where T_limit <Tg, where Tg is the glass transition temperature of the polymer or polymer mixture present in the suspension. In a preferred embodiment, the upper temperature limit is defined as T_limit <Tg-20 K and in a particularly preferred embodiment T_limit <Tg-40K is the upper temperature limit.

In a further embodiment, the dried mixture obtained in step B) is then suspended in a suspension medium. The active substance content may be ≥50% by weight, preferably ≥60% by weight, based on the total weight of the dry substance.

In a further embodiment, the suspension medium is an aqueous suspension medium. Preference is given to using water without further additives.

The invention further relates to a pharmaceutical formulation comprising a pharmaceutical active substance coated with an at least partially water-soluble polymer, wherein the pharmaceutical active substance is present in the form of particles having a $d_{90}$ value in the particle size distribution of ≤1 μm and the polymer additionally comprises an ionic surfactant. This formulation may be obtained by a process according to the invention. The embodiments of the process elucidated above are accordingly also applicable to the formulation.

A further aspect of the invention is a suspension of a pharmaceutical active substance that is obtainable by a process according to the invention.

EXAMPLES

The present invention is elucidated in detail by the examples and figures that follow, but without being restricted thereto. The abbreviation "wt %" means percent by weight and is based on the total weight of the aqueous suspension. PVP K12 is a polyvinylpyrrolidone having a Fikentscher K value (DIN EN ISO 1628-1) of 12. SDS is sodium dodecyl sulfate. KVA 64 is Kollidon® VA64, a vinylpyrrolidone-vinyl acetate copolymer.

Example 1: Freeze-Drying of Indometacin-PVP
K12-SDS Nanosuspensions

The nanosuspension was prepared using a planctary ball mill (Fritsch Pulverisette 5). For this, 10 wt % of indometacin was stabilized with 6 wt % of PVP K12 and 0.1 wt % of SDS. The polymer-surfactant solutions were prepared and dissolved separately. The solution was then mixed with indometacin powder and the resulting suspension homogenized on a stirring plate. The milling compartments were filled 60% (by volume) with 0.4-0.6 mm milling beads (SiLibeads, zirconium oxide, yttrium-stabilized) and the remaining volume was filled with suspension, taking care to exclude air bubbles. After milling for 1 h 30 min at 400 rpm, a nanosuspension containing particles having a $d_{90}$<500 nm (Malvern, Mastersizer 2000) was present that could be used for drying.

For freeze-drying, 3 ml vials were filled with 0.7 g of suspension (filling level <1 cm) and placed in the freeze-dryer, which was precooled to −40° C. The "solid cakes" obtained after drying were crushed into powder with a spatula and wetted with water. The resulting suspension was then measured by static light scattering (Malvern, Mastersizer 2000) and compared with the particle size distribution of the original suspension after milling (FIG. 1). The suspensions, which contained 0.1 wt % of SDS and 6 wt % of PVP K12, showed almost complete redispersibility (10 wt % of indometacin). The resulting active substance content of the redispersible powders containing active substance nanoparticles was over 60 wt %.

FIG. 1 shows the particle size distribution before drying (after milling) and after redispersion (X=1.120).

Figure 2:
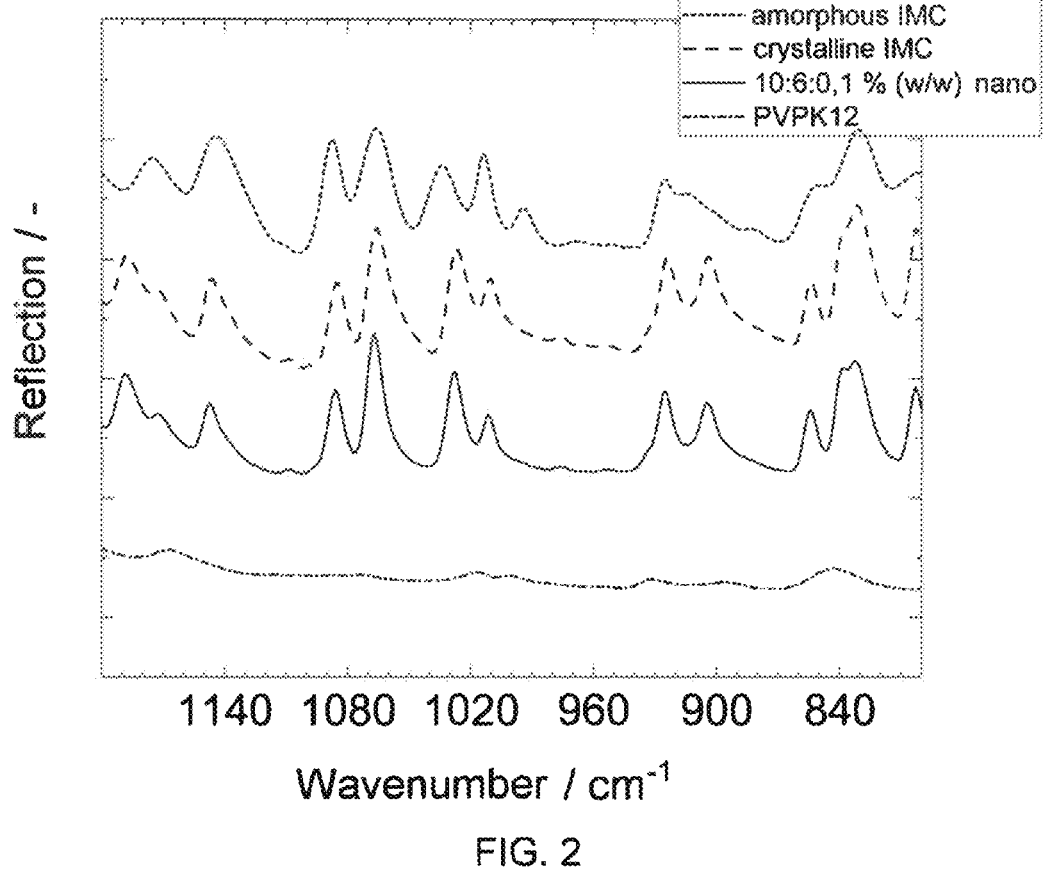
Figure 3:
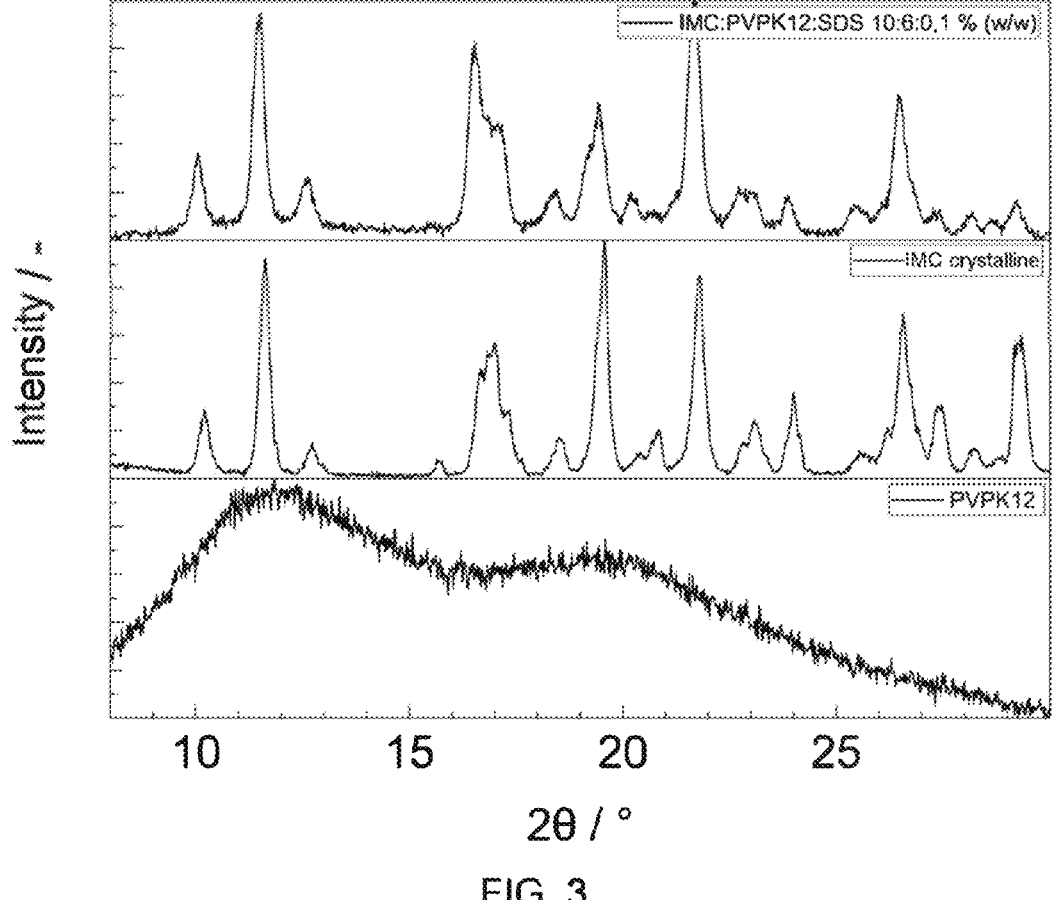

The powders containing nanoparticles were additionally examined by Fourier transform infrared spectroscopy (FTIR, FIG. 2) and X-ray powder diffractometry (XRPD, FIG. 3). It can be seen that the crystalline state of the indometacin particles was maintained.

Example 2: Freeze-Drying of Indometacin-KVA 64-SDS Nanosuspensions

Figure 4:
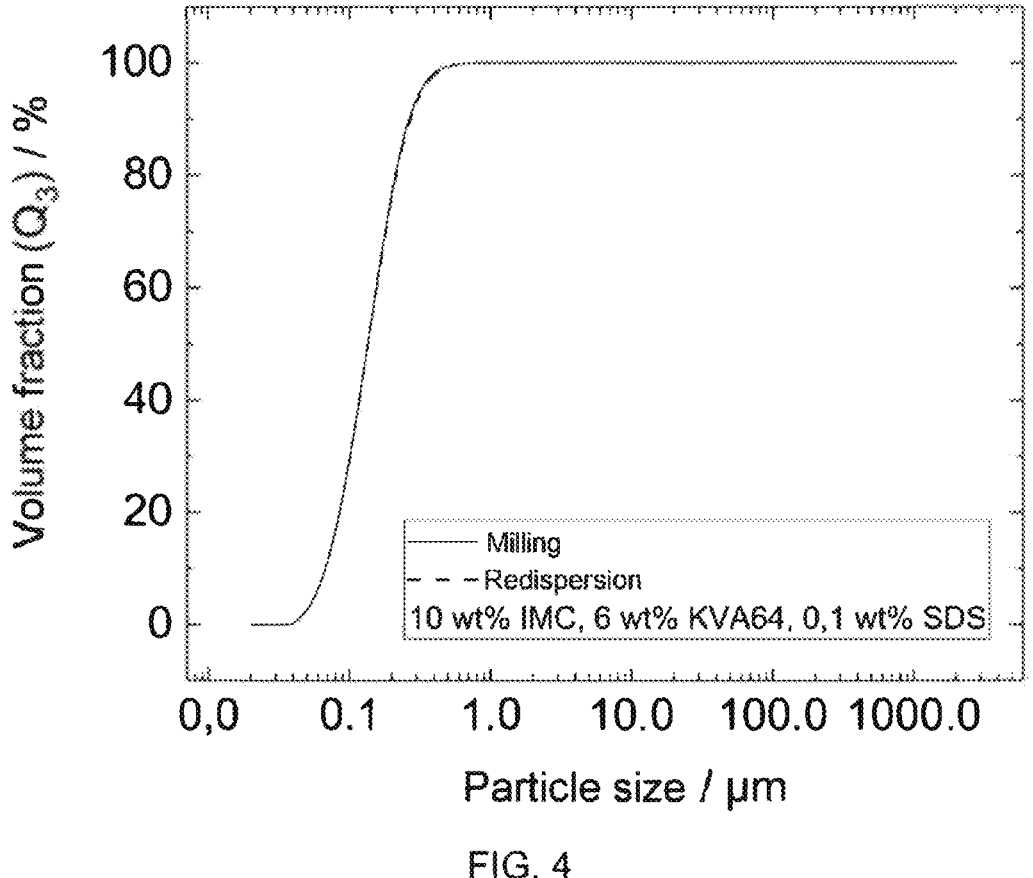

The nanosuspension was prepared in analogous manner to example 1, except that the polymer KVA 64 was used instead of PVP K12 (10:6:0.1 wt % active substance: polymer: SDS). For freeze-drying, 3 ml vials werc filled with 0.7 g of suspension (filling level <1 cm) and placed in the freeze-dryer, which was precooled to −40° C. The "solid cakes" obtained after drying were crushed into powder with a spatula and wetted with water. The resulting suspension was then measured by static light scattering (Malvern, Mastersizer 2000) and compared with the particle size distribution of the original suspension after milling (FIG. 4). The suspensions, which contained 0.1 wt % of SDS and 6 wt % of KVA 64, showed almost complete redispersibility (10 wt % of indometacin). The resulting active substance content of the redispersible powders containing active substance nanoparticles was over 60 wt %.

FIG. 4 shows the particle size distribution before drying (after milling) and after redispersion (X=1.022).

Figure 5:
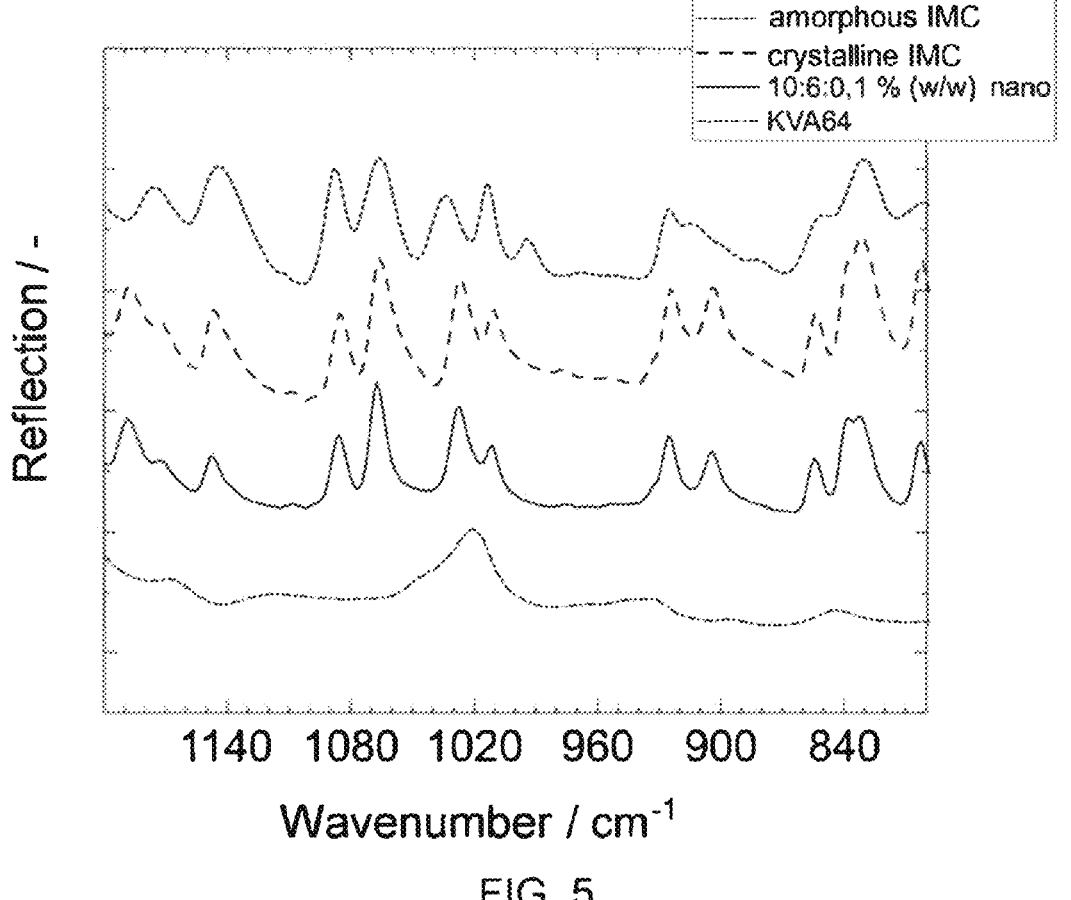
Figure 6:
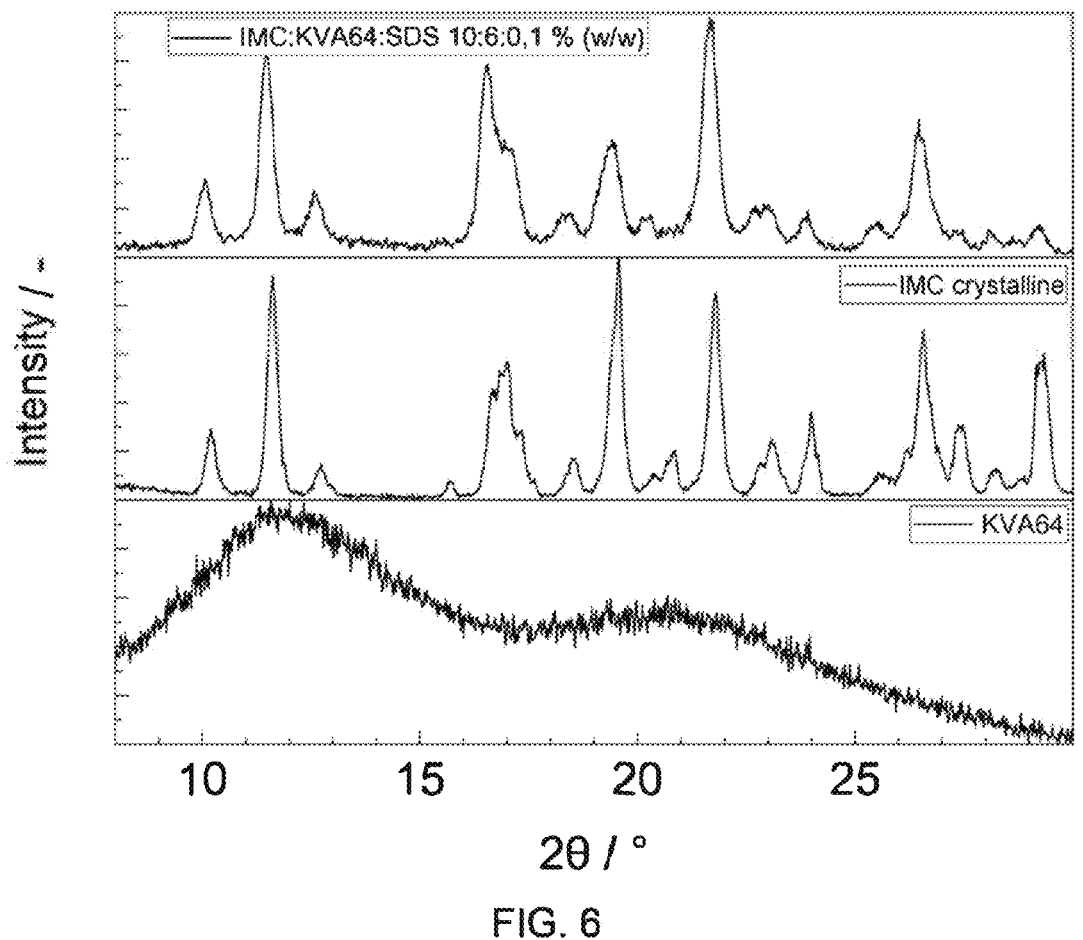

The powders containing nanoparticles were additionally examined by Fourier transform infrared spectroscopy (FTIR, FIG. 5) and X-ray powder diffractometry (XRPD, FIG. 6). It can be seen that the crystalline state of the indometacin particles was maintained.

Example 3: Freeze-Drying of Vericiguat-PVP K12-SDS Nanosuspensions

Figure 7:
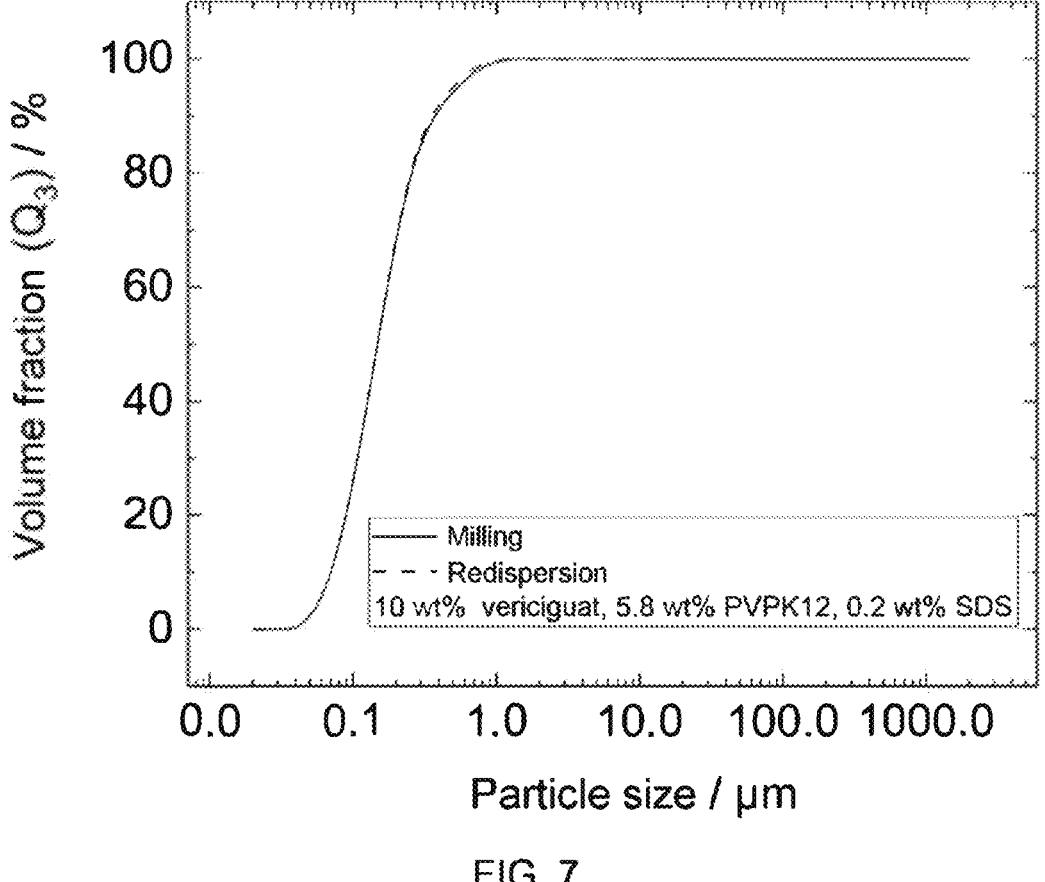

The nanosuspension was prepared in analogous manner to example 1, except that vericiguat was used instead of indometacin and different concentration ratios were present (10:5.8:0.2 wt % active substance: polymer: SDS). For freeze-drying, 3 ml vials were filled with 0.7 g of suspension (filling level <1 cm) and placed in the freeze-dryer, which was precooled to −40° C. The "solid cakes" obtained after drying were crushed into powder with a spatula and wetted with water. The resulting suspension was then measured by static light scattering (Malvern, Mastersizer 2000) and compared with the particle size distribution of the original suspension after milling (FIG. 7). The suspensions, which contained 0.2 wt % of SDS and 5.8 wt % of PVP K12, showed almost complete redispersibility (10 wt % of vcriciguat). The resulting active substance content of the redispersible powders containing active substance nanoparticles was over 60 wt %.

FIG. 7 shows the particle size distribution before drying (after milling) and after redispersion.

Figure 8:
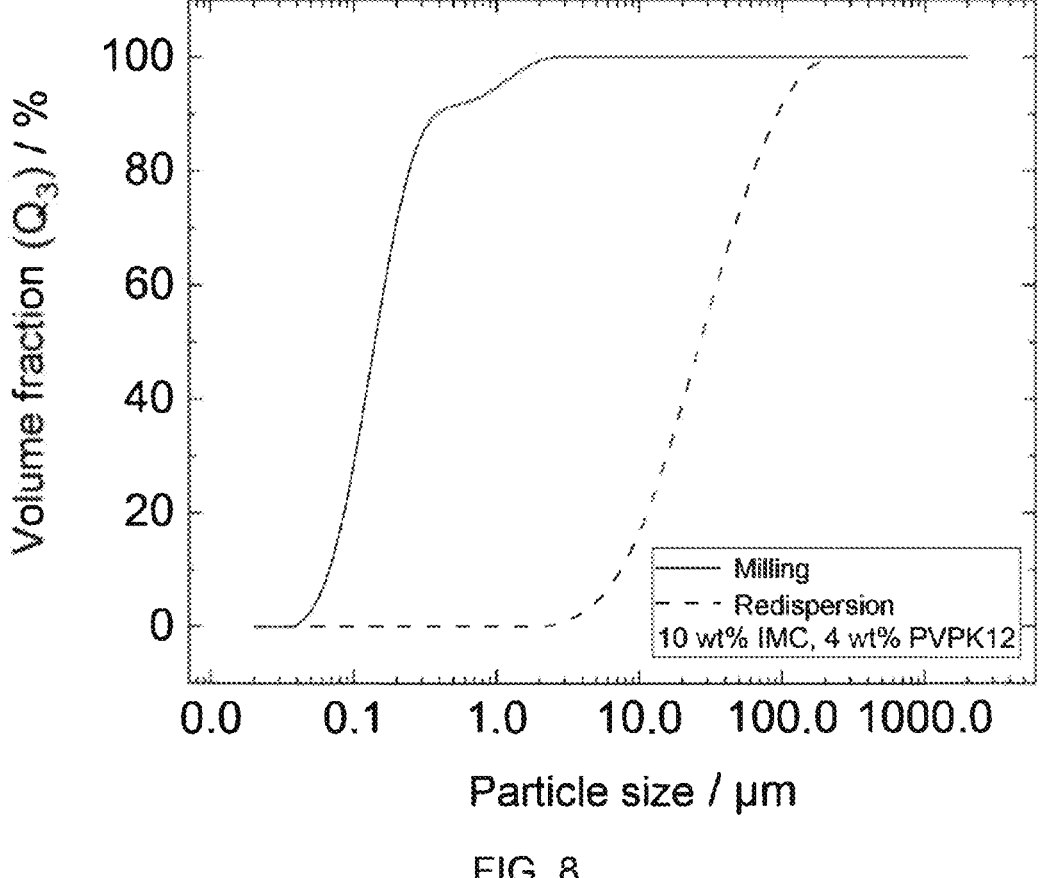

Comparative Example: Freeze-Drying of Indometacin-PVP K12 Nanosuspensions Without Surfactant The nanosuspension was prepared in analogous manner to example 1, except that the surfactant was omitted altogether. This had no great effect on the outcome of milling, consequently stable production of particles <500 nm was possible here too. For freeze-drying, 3 ml vials were filled with 0.7 g of suspension (filling level <1 cm) and placed in the freeze-dryer, which was precooled to −40° C. The "solid cakes" obtained after drying were crushed into powder with a spatula and wetted with water. The resulting suspension was then measured by static light scattering (Malvern, Mastersizer 2000) and compared with the particle size distribution of the original suspension after milling (FIG. 8). These suspensions did not show adequate redispersibility irrespective of the polymer content (10 wt % of active substance). FIG. 8 shows the particle size distribution before drying (after milling) and after redispersion (X=242.823).

Example 4—Longer Milling Times Result in Improved Redispersibility

Figure 9:
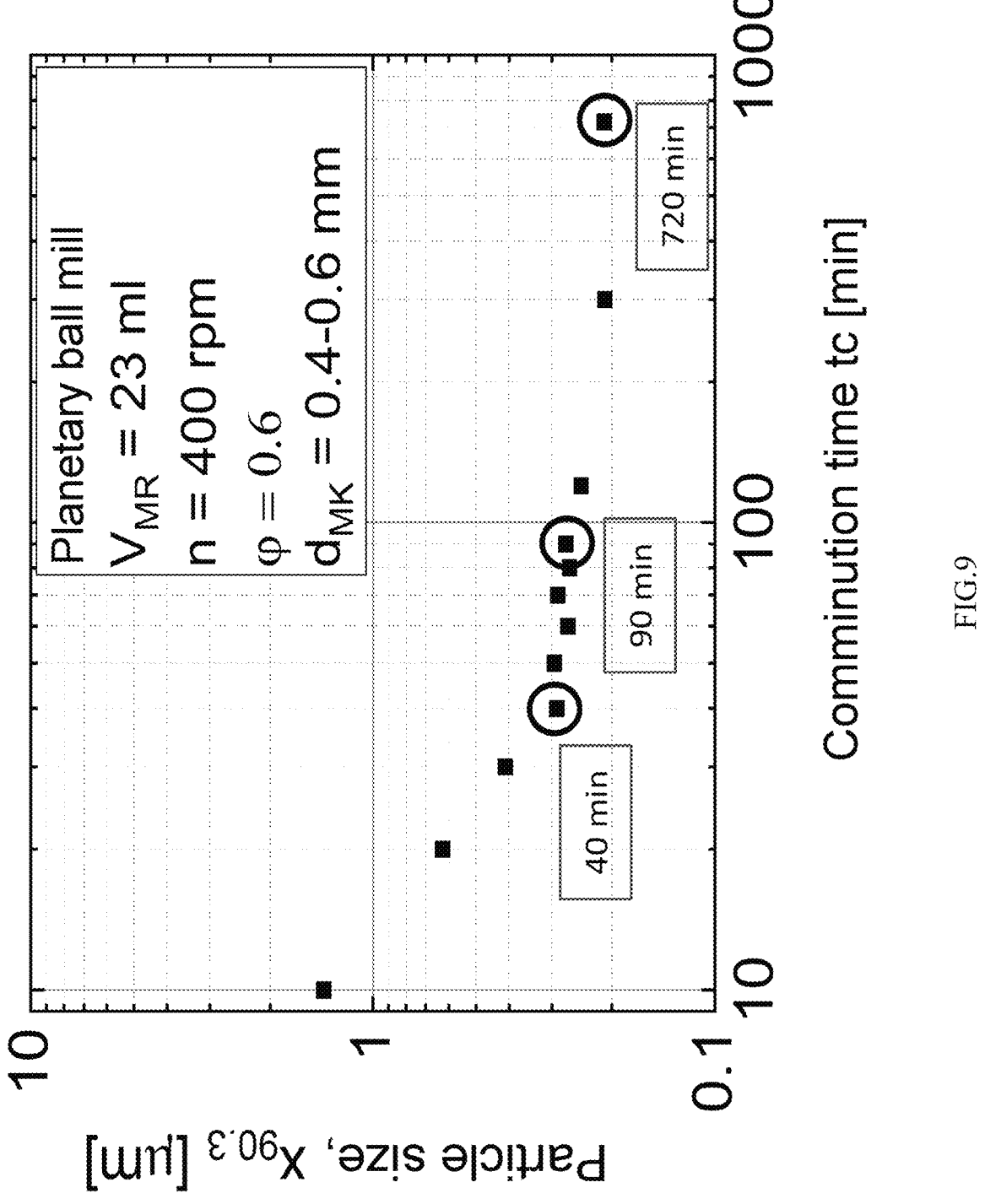

The nanosuspension was prepared using a planetary ball mill (Fritsch Pulverisette 5). For this, 9 wt % of indometacin was stabilized with 9 wt % of PVP K12 and 0.2 wt % of SDS. The polymer-surfactant solutions were prepared and dissolved separately. The solution was then mixed with indometacin powder and the resulting suspension homogenized on a stirring plate. The milling compartments were filled 60% (by volume) with 0.4-0.6 mm milling beads (SiLibeads, zirconium oxide, yttrium-stabilized) and the remaining volume was filled with suspension, taking care to exclude air bubbles. After milling times of 40 min, 90 min and 720 min at 400 rpm, suspensions having similar d(90) values were present (cf. FIG. 9). The three suspensions were dried by spray-drying (4M8-Trix ProCept) The inlet temperature was 110° C. A two-substance nozzle having a diameter of 1.2 mm was used.

Figure 10:
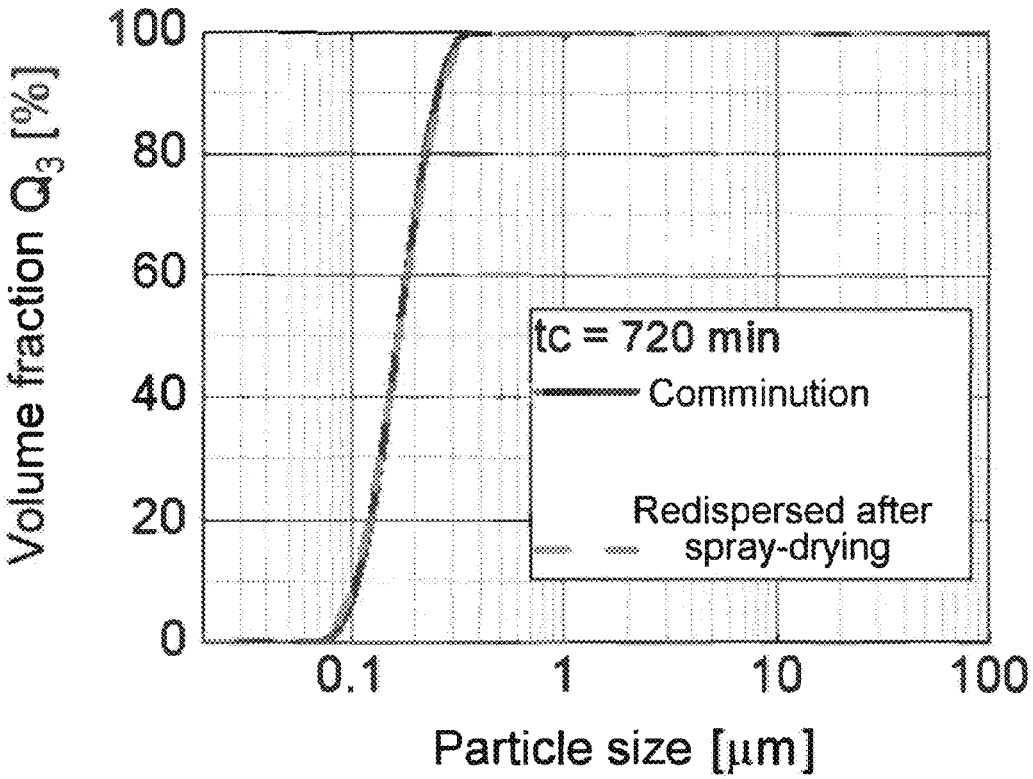
Figure 11:
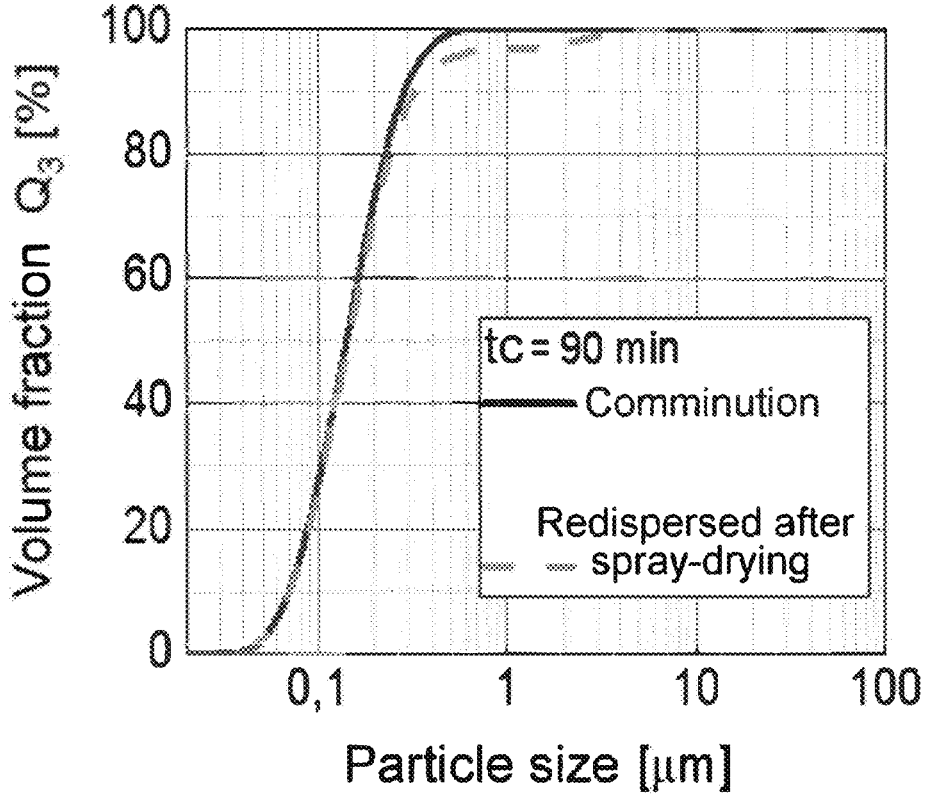
Figure 12:
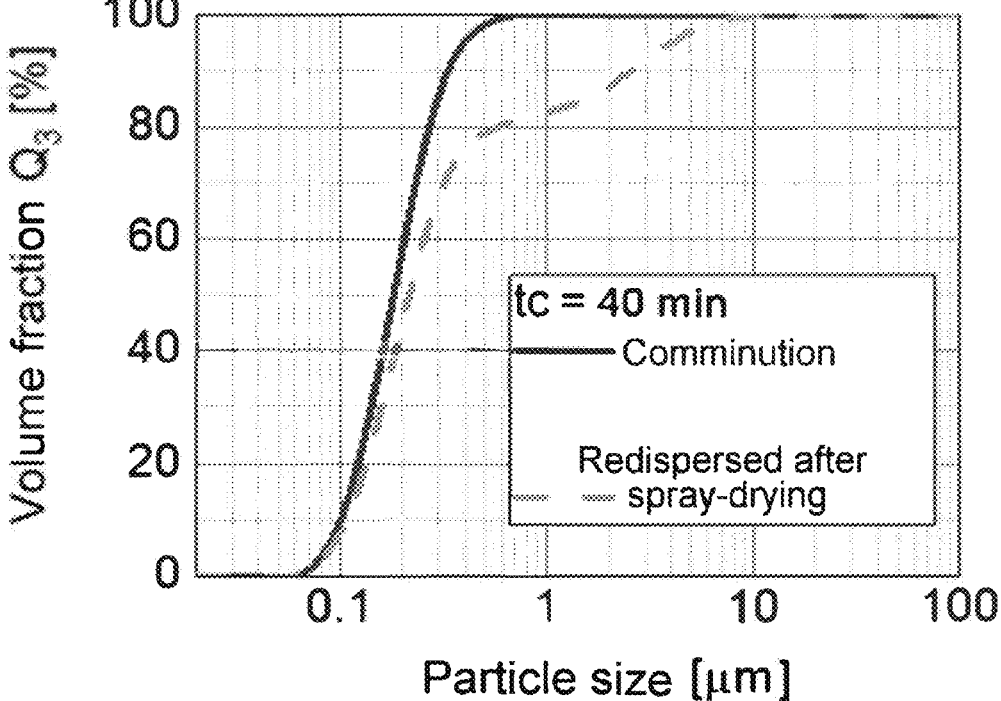

The resulting powders were dispersed with the same amount of water that was present in the suspension before drying, which meant that the suspensions obtained had concentration ratios identical to those after milling. The particle size distribution of the suspensions after drying and redispersion was compared with that of the suspensions before drying. It can be seen clearly that a longer milling time results in powders having better redispersibility (FIGS. 10-12). Thus, after drying and redispersion, the particle size distribution (PSD) of the suspension milled for 40 min (tc=40 min) shows clear differences from the PSD of the original suspension (cf. FIG. 12). After tc=90, an improvement in redispersibility can already be seen (FIG. 11). By contrast, after drying and redispersion the suspension milled for 720 min (tc=720 min) shows no differences in PSD from the PSD of the original suspension and thus matches the latter completely (cf. FIG. 10).

Figure 13:
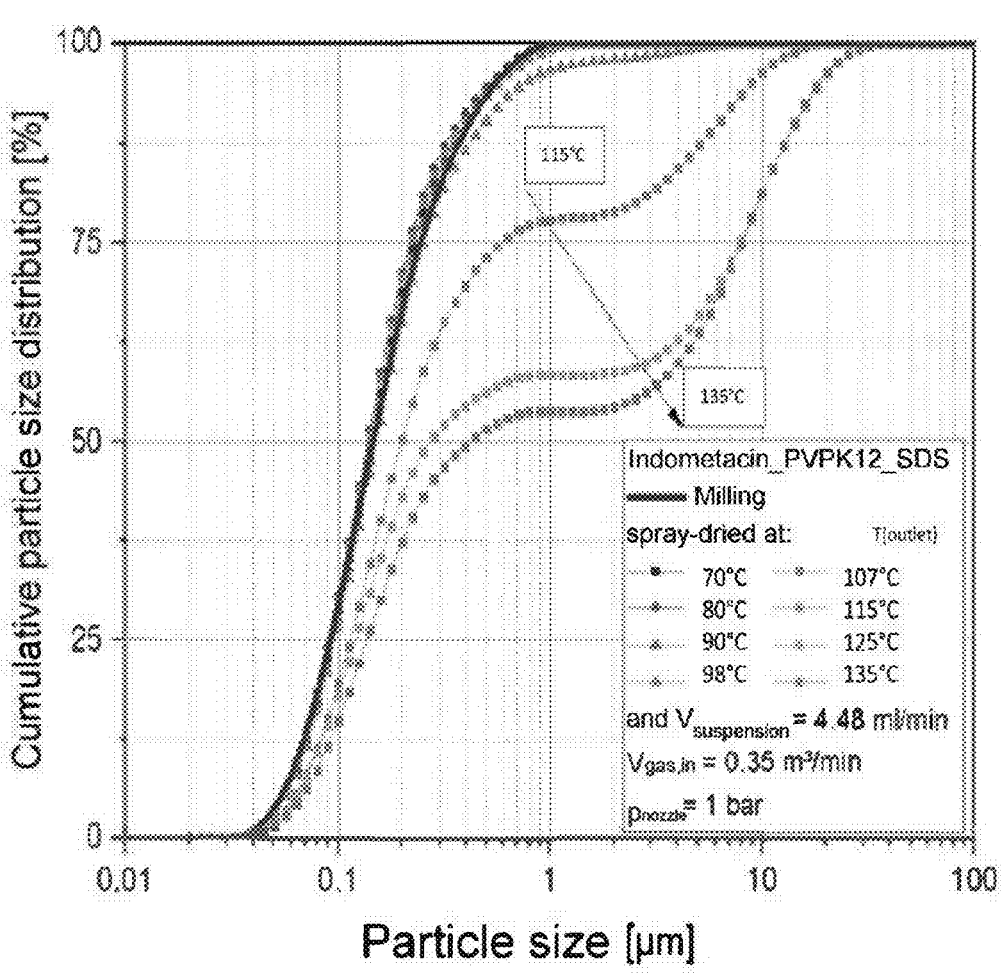

Example 5—Low Drying Temperatures During Spray-Drying Result in Improved Redispersibility The nanosuspension was prepared using a planetary ball mill (Fritsch Pulverisette 5). For this, 9 wt % of indometacin was stabilized with 9 wt % of PVP K12 and 0.1 wt % of SDS. The polymer-surfactant solutions were prepared and dissolved separately. The solution was then mixed with indometacin powder and the resulting suspension homogenized on a stirring plate. The milling compartments were filled 60% (by volume) with 0.4-0.6 mm milling beads (SiLibeads, zirconium oxide, yttrium-stabilized) and the remaining volume was filled with suspension, taking care to exclude air bubbles. After milling for 90 min at 400 rpm, a nanosuspension containing particles having a $d_{90}$<500 nm (Malvern, Mastersizer 2000) was present that could be used for drying. The suspension was dried with the spray-dryer (from ProCepT, model 4M8-TriX) at temperatures from 70° C. to 135° C. The temperatures stated are the gas-outlet temperatures of the spray-dryer and therefore correspond also to the highest possible product temperatures. The volume flow of the suspension was 4.48 ml/min and the volume flow of the dry gas was 0.35 m$^3$/min. The suspension was atomized at a nozzle pressure of 1 bar. FIG. 13 shows the particle size distributions of the respective suspensions after drying at various temperatures and subsequent redispersion. The temperatures stated correspond to the resulting gas-outlet temperatures. It can be seen clearly that complete redispersibility of the dried powder is achieved up to a temperature of 98° C. This is evident from the fact that the particle size distribution (PSD) of the redispersed powder corresponds to the PSD of the suspension before drying and that is characterized by "milling". At a temperature of 107° C., the redispersibility is still almost unchanged. However, at temperatures of 115° C. and above there is a tendency to increased agglomerate formation, which adversely affects the redispersibility of the dried powder and is reflected in the PSD as a consequence of the presence of larger particles. The glass transition temperature of the polymer is approx. 112° C. A drying temperature below the glass transition temperature of the polymer is thus shown to be beneficial to the complete redispersibility of powders obtained when drying by means of spray-drying.

The invention claimed is:

1. A process for producing a pharmaceutical formulation comprising:
   A) providing a pharmaceutical active substance;
   B) milling the pharmaceutical active substance to obtain particles of the pharmaceutical active substance, wherein the pharmaceutical active substance is milled for a milling time, wherein the milling time, which is the residence time of the pharmaceutical active substance in a mill, is at least 1.5 times the time required to mill the particles such that the $d_{90}$ of the particle size distribution PSD) is 1.5 times the $d_{90}$ value reached after 12 hours;
   C) suspending the particles of the pharmaceutical active substance in an aqueous solution of a polymer;
   D) contacting the particles of the pharmaceutical substance with an ionic surfactant; and
   E) drying the mixture obtained in D) after the addition of ionic surfactant;
   wherein,
   in C), the pharmaceutical active substance is present in the form of particles having a $d_{90}$ value in a particle size distribution (PSD) of ≤1 µm,
   wherein the particles of the pharmaceutical active substance are not contacted with a sugar or sugar alcohol,
   wherein the pharmaceutical active substance and the polymer are present in a relative weight ratio of ≥1:2 to ≤5:1, and
   wherein the polymer and the ionic surfactant are present in a relative weight ratio of ≥40:1 to ≤100:1.

2. A process according to, claim 1, wherein the ionic surfactant is selected from the group consisting of: acylamino acids and salts thereof, carboxylic acids and derivatives, sulfonic acids and sulfonate salts, sulfuric esters, alkylamines, alkylimidazoles, ethoxylated amines, quaternary surfactants, esterquats, and a mixture thereof.

3. The process according to claim 1, wherein the drying in E) is effected by freeze-drying.

4. The process according to claim 1, wherein the drying in E) is effected by means of contact drying or by a process comprising spraying of the mixture.

5. The process according to claim 4, wherein the process comprising spraying of the mixture from an outlet which is at an outlet temperature, and wherein said outlet temperature is lower than a glass transition temperature of the polymer present in the mixture.

6. The process according to claim 5, wherein the outlet temperature is more than 20K below the glass transition temperature of the polymer present in the mixture.

7. The process according to claim 5, wherein the outlet temperature is more than 40K below the glass transition temperature of the polymer present in the mixture.

8. The process according to claim 1, further comprising suspending the dried mixture obtained in E) in a suspension medium.

9. The process of claim 1, wherein the milling time is at least 2 times the time required to mill the particles such that the $d_{90}$ of the particle size distribution (PSD) is 1.5 times the $d_{90}$ value reached after 12 hours.

10. The process of claim 9, wherein the milling time is at least 4 times the time required to mill the particles such that the $d_{90}$ of the particle size distribution (PSD) is 1.5 times the $d_{90}$ value reached after 12 hours.

* * * * *